United States Patent
Steinert

(10) Patent No.: US 10,191,073 B2
(45) Date of Patent: Jan. 29, 2019

(54) APPARATUS AND METHOD FOR PROCESSING AT LEAST ONE SAMPLE

(71) Applicant: Roche Diagnostics Operations, Inc., Indianapolis, IN (US)

(72) Inventor: Chris Steinert, Lucerne (CH)

(73) Assignee: Roche Diagnostics Operations, Inc., Indianapolis, IN (US)

( * ) Notice: Subject to any disclaimer, the term of this patent is extended or adjusted under 35 U.S.C. 154(b) by 197 days.

(21) Appl. No.: 15/268,764

(22) Filed: Sep. 19, 2016

(65) Prior Publication Data

US 2017/0097370 A1 Apr. 6, 2017

(30) Foreign Application Priority Data

Oct. 6, 2015 (EP) ..................................... 15188559

(51) Int. Cl.
*G01N 35/00* (2006.01)
*G01N 35/02* (2006.01)
(Continued)

(52) U.S. Cl.
CPC ..... *G01N 35/0095* (2013.01); *G01N 35/0099* (2013.01); *G01N 35/025* (2013.01); *G01N 35/026* (2013.01); *G01N 35/10* (2013.01); *G01N 35/1004* (2013.01); *G01N 2035/00524* (2013.01); *G01N 2035/041* (2013.01); *G01N 2035/0413* (2013.01); *G01N 2035/0441* (2013.01); *G01N 2035/0444* (2013.01);
(Continued)

(58) Field of Classification Search
CPC ............. G01N 35/0095; G01N 35/026; G01N 35/0099; G01N 35/025; G01N 35/10; G01N 35/1004; G01N 2035/0446; G01N 2035/00524; G01N 2035/041; G01N 2035/0413; G01N 2035/0441; G01N 2035/0444; G01N 2035/0465
See application file for complete search history.

(56) References Cited

U.S. PATENT DOCUMENTS

| 4,609,017 A | 9/1986 | Coulter et al. |
| 6,544,476 B1 | 4/2003 | Mimura et al. |

(Continued)

FOREIGN PATENT DOCUMENTS

| CA | 1199258 A | 1/1986 |
| EP | 2306171 A2 | 4/2011 |
| JP | 2013-167650 A | 8/2013 |

*Primary Examiner* — Samuel P Siefke
(74) *Attorney, Agent, or Firm* — Roche Diagnostics Operations, Inc.

(57) ABSTRACT

A method and apparatus for processing a sample is presented. The apparatus comprises a chamber, a first input for inputting a first vessel into the chamber, a second input for inputting a second vessel into the chamber, the second input is different from the first input, a rotor comprising a first compartment for receiving the first vessel and a second compartment for receiving the second vessel, a gripper to grip the first vessel and to transport the first vessel to the first compartment, and a pipettor to pipette a sample from the first vessel and/or second vessel. The rotor rotates between a first position where the first vessel is transportable to the first compartment by the gripper, a second position where the second vessel is loadable into the second compartment, and a third position where the sample of the first vessel and/or second vessel is aspiratable by the pipettor.

17 Claims, 15 Drawing Sheets

(51) Int. Cl.
   *G01N 35/10*   (2006.01)
   *G01N 35/04*   (2006.01)
(52) U.S. Cl.
   CPC ................ *G01N 2035/0446* (2013.01); *G01N 2035/0465* (2013.01)

(56) References Cited

U.S. PATENT DOCUMENTS

2006/0245865 A1   11/2006   Babson
2009/0227033 A1   9/2009   Hamada et al.
2013/0019697 A1   1/2013   McKeen et al.
2015/0079695 A1   3/2015   Pollack et al.

APPARATUS AND METHOD FOR PROCESSING AT LEAST ONE SAMPLE

CROSS-REFERENCE TO RELATED APPLICATIONS

This application claims priority to EP 15188559.7, filed Oct. 6, 2015, which is hereby incorporated by reference.

BACKGROUND

The present disclosure relates to an apparatus and a method for processing at least one sample.

An apparatus for processing at least one sample, particularly analytical instruments and more particularly medical instruments, serve to process samples in order to allow the samples to be analyzed. Such samples include but are not limited to body fluids which are examined, especially blood or any other liquid reagents used in the medical field. Modern apparatus of this kind are largely fully automatic in operation and only the samples stored in reagent vessels have to be inserted into the apparatus and the desired analysis has to be entered.

The present disclosure is intended for apparatuses which operate with liquids reagents contained in the reagent vessels which may be made of plastics. The apparatus usually have an input for inputting a vessel into a processing chamber where the intended processing such as an analysis is carried out. Automated apparatus process a plurality of vessels such as five or eight vessels which are input in a so-called rack. The vessels are processed in a subsequent order.

It may be the case that a further sample is intended to be processed before all of the samples input by the rack are processed. Particularly, hematology is critical in terms of time as whole blood has to be re-suspended as promptly as possible to the measurement because blood particles sediment fast.

Using the above-described apparatus for processing a sample provides advantages concerning the handling. Nevertheless, there are still some drawbacks. For this reason, apparatus have been provided which allow for the manually input of a further sample. For example a so-called STAT sample (STAT=short turn around time) can be loaded manually into a carrier at the bottom of an input stack. Such loading of a STAT tube causes another tube to be removed from its carrier. Thus, such a single tube input interrupts the automated input reducing the throughput of the apparatus. Further, users have to wait a significant period of time until the single tube inlet is accessible after request.

Another known apparatus comprises a first input for inputting a first vessel and a separate second input for inputting a second vessel into a processing chamber. The first and second vessels may be linearly moved in all three dimensions of space to a processing position in the processing chamber. Thus, this apparatus uses several linear axes increasing the manufacturing costs of the apparatus. Further, the coordination of the handling of the different samples along the linear axes is rather complex.

Therefore, there is a need for an apparatus for processing a sample allowing processing of not only automatically input vessels but also STAT vessels, which are to be processed with a higher priority than the automatically input vessels, such that the manufacturing costs are decreased and the workflow is improved or accelerated.

SUMMARY

According to the present disclosure, a method and apparatus for processing at least one sample are presented. The apparatus can comprise a processing chamber, a first input for inputting at least a first vessel into the processing chamber, and a second input for inputting at least a second vessel into the processing chamber. The second input can be different from the first input. The apparatus can further comprise a rotor comprising at least a first compartment for receiving the first vessel from the first input and a second compartment for receiving the second vessel from the second input; a gripping device adapted to at least grip the first vessel and to transport the first vessel from the first input to the first compartment of the rotor; and a pipetting device adapted to at least pipette a sample from the first vessel and/or the second vessel. The rotor can be rotatable at least between a first processing position, at which the first vessel is transportable to the first compartment of the rotor by the gripping device, a second processing position, at which the second vessel is loadable into the second compartment of the rotor from the second input, and a third processing position, at which the sample of the first vessel and/or the second vessel is aspiratable by the pipetting device.

Accordingly, it is a feature of the embodiments of the present disclosure to provide for an apparatus for processing a sample allowing processing of not only automatically input vessels but also STAT vessels, which are to be processed with a higher priority than the automatically input vessels, such that the manufacturing costs are decreased and the workflow is improved or accelerated. Other features of the embodiments of the present disclosure will be apparent in light of the description of the disclosure embodied herein.

BRIEF DESCRIPTION OF THE SEVERAL VIEWS OF THE DRAWINGS

The following detailed description of specific embodiments of the present disclosure can be best understood when read in conjunction with the following drawings, where like structure is indicated with like reference numerals and in which.

DETAILED DESCRIPTION

Figure 1:
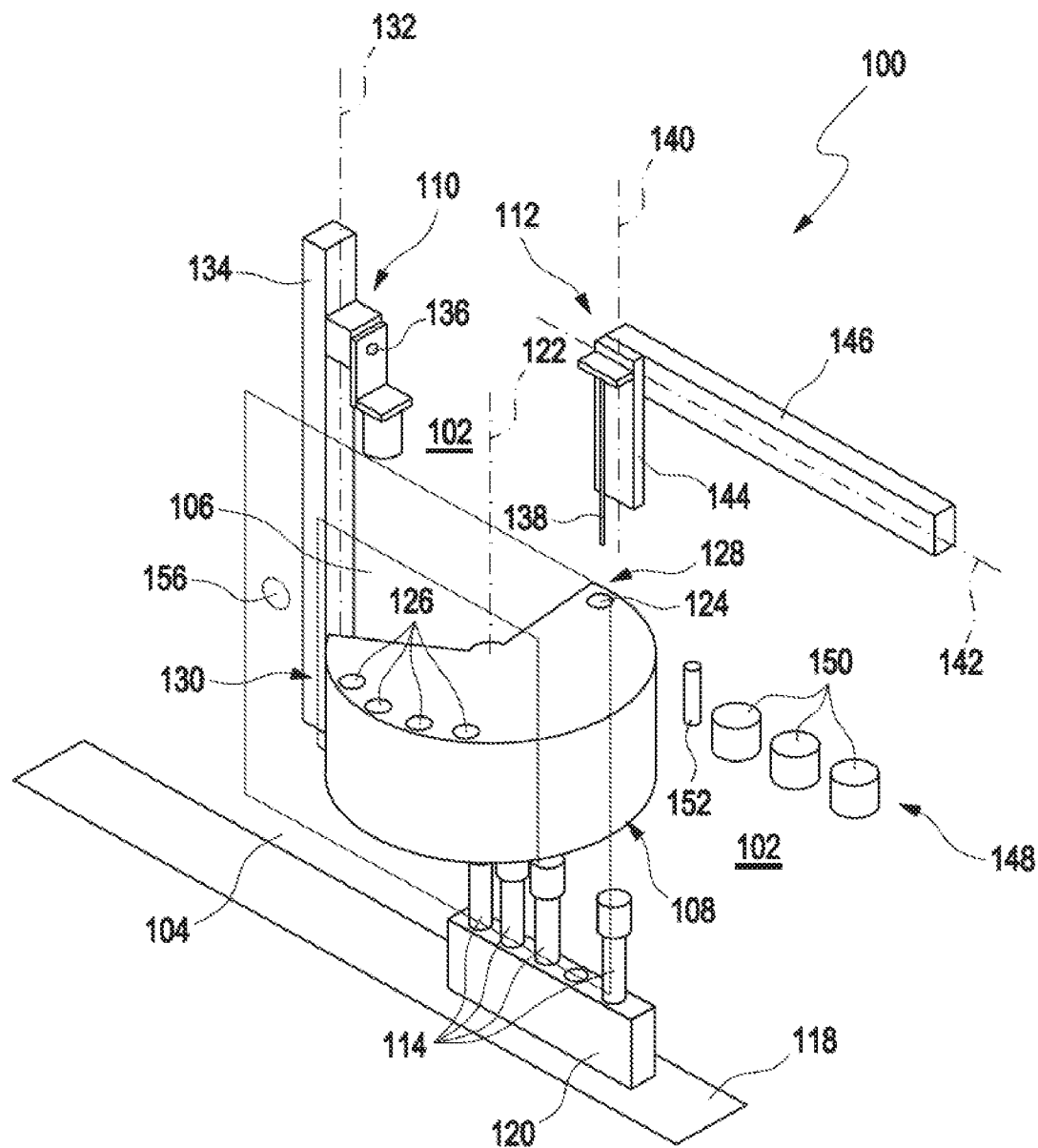
FIG. 1 illustrates a perspective view of an apparatus for processing at least one sample in a first operation position according to an embodiment of the present disclosure.

In the following detailed description of the embodiments, reference is made to the accompanying drawings that form a part hereof, and in which are shown by way of illustration, and not by way of limitation, specific embodiments in which the disclosure may be practiced. It is to be understood that other embodiments may be utilized and that logical, mechanical and electrical changes may be made without departing from the spirit and scope of the present disclosure.

As used in the following, the terms "have", "comprise" or "include" or any arbitrary grammatical variations thereof are used in a non-exclusive way. Thus, these terms may both refer to a situation in which, besides the feature introduced by these terms, no further features are present in the entity described in this context and to a situation in which one or more further features are present. As an example, the expressions "A has B", "A comprises B" and "A includes B" may both refer to a situation in which, besides B, no other element is present in A (i.e. a situation in which A solely and exclusively consists of B) and to a situation in which, besides B, one or more further elements are present in entity A, such as element C, elements C and D or even further elements.

Further, it shall be noted that the terms "at least one", "one or more" or similar expressions indicating that a feature or element may be present once or more than once typically will be used only once when introducing the respective feature or element. In the following, in most cases, when referring to the respective feature or element, the expressions "at least one" or "one or more" will not be repeated, non-withstanding the fact that the respective feature or element may be present once or more than once.

Further, as used in the following, the terms "first", second", "third" and the like are exclusively used to linguistically distinguish between the respective constructional members associated with these terms and are not intended to give a certain order of importance.

An apparatus for processing at least one sample is disclosed. The apparatus can comprise a processing chamber, a first input for inputting at least a first vessel into the processing chamber, a second input for inputting at least a second vessel into the processing chamber. The second input can be different from the first input. The apparatus can also comprise a rotor comprising at least a first compartment for receiving the first vessel from the first input and a second compartment for receiving the second vessel from the second input, a gripping device adapted to at least grip the first vessel and to transport the first vessel from the first input to the first compartment of the rotor, and a pipetting device at least adapted to pipette a sample from the first vessel and/or the second vessel. The rotor can be rotatable at least between a first processing position, at which the first vessel is transportable to the first compartment of the rotor by the gripping device, a second processing position, at which the second vessel is loadable into the second compartment of the rotor from the second input, and a third processing position, at which the sample of the first vessel and/or the second vessel is aspiratable by the pipetting device.

The two different inputs can allow input into vessels with different priority for the processing or handling. The rotor can significantly decrease the number of linear axes. Further, the rotational axis, instead of linear axes, can be less expensive and can simplify construction. The rotor can allow transfer to the respective different vessels to the target positions without the transporting paths conflicting or obstructing each other. Thus, the first vessel may be transported from the first processing position to the third processing position or the second vessel may be transported from the second processing position to the third processing position without the necessity of complex moving paths. At the third processing position, the pipetting device may aspirate the sample from the first vessel and the second vessel, respectively.

The second input may be located at the rotor. Thus, an operator may load the second vessel directly into the second compartment of the rotor without any transporting device between the second input and the rotor.

The gripping device may be adapted to rock the first vessel and/or the second vessel. Thus, any samples of the first vessel and/or the second vessel may be suspended.

The gripping device may be moveable along a first axis. Thus, by a linear movement such as an upward or downward movement, the first vessel may be gripped so as to be transported to the rotor or vice versa.

The second compartment may be different from the first compartment. Thus, any mixing of the samples within the intended analysis or processing is prevented.

The rotor may be rotatable around a rotational axis. The first compartment can be located at a first angular position with respect to the rotational axis. The second compartment can be located at a second angular position with respect to the rotational axis. The second angular position can be different from the first angular position. Thus, the first compartment and the second compartment may be transferred to the respective processing positions by a simple rotational movement.

The second compartment may be separated from the first compartment. Thus, an unwanted loading of the second vessel into the first compartment by an operator may be prevented which can also prevent a mixing of the respective samples within the analysis.

The second compartment may be separated from the first compartment by a separating wall. Thus, the first compartment may not be exposed to an operator.

The second compartment may be located adjacent the first compartment. Thus, the respective processing positions can be arranged close to one another which can minimize the time for transporting the respective vessels between the respective processing positions.

The pipetting device may move along a second axis and along a third axis. The third axis can be different from the second axis. Thus, by a movement within a single plane, the pipetting device may process the samples from the respective vessels.

The third axis may be substantially perpendicular to the second axis. Thus, moving paths of the pipetting device can rather be simply controllable as two linear movements are well known to be controlled.

The second axis may be substantially parallel to the first axis. Thus, the gripping device and the pipetting device may be moved substantially parallel to one another which can prevent any conflicts of the respective movement paths.

The pipetting device may be moveable along the first axis. Thus, the gripping device and the pipetting device may be moved on the same axis which can minimize the space required for operating the same.

The pipetting device can move together with the gripping device along the first axis. Thus, a single drive may be sufficient to move the pipetting device and the gripping device.

The pipetting device may be adapted to dispense the sample of the first vessel and/or the second vessel at a processing station within the processing chamber. Thus, the operation of the pipetting device can allow further process of the sample of the first vessel and/or the second vessel.

The processing station may be located spaced apart from the rotor. Thus, a movement of the processing station may be omitted as the samples are transported to the processing station by the rotor.

Alternatively, the processing station may be arranged on the rotor. Thus, the space required for the rotor and the processing station can be minimized.

The rotor may be formed as a segment of a cylinder. Thus, the rotor may not obstruct the movement paths of the gripping device and the pipetting device.

The processing chamber may comprise a closure. The closure can be adapted to selectively expose or block the second input. Thus, an unwanted exposition of the second input during a processing of a vessel within the processing chamber may be prevented.

The first input can comprise a transporting device for automatically transporting at least the first vessel. Thus, the first input may be automatically supplied with the first vessel.

The transporting device can be linearly moveable. Thus, the first input may be automatically supplied with the first vessel by a simple linear movement of the transporting device.

The transporting device may be adapted to transport a rack. The rack can be adapted to receive a plurality of vessels. Thus, the first input may be automatically supplied with a plurality of vessels which can increase the throughput of the apparatus.

The rotor may comprise a plurality of compartments for receiving a plurality of vessels. Thus, the throughput of the apparatus may be further increased. Further, the compartment may comprise compartments of different sizes which allows to process vessels of different sizes.

A method for processing at least one sample using an apparatus as described is disclosed. The method can comprise inputting at least a first vessel into the processing chamber through the first input, retrieving the first vessel from the first input by the gripping device, rotating the rotor into the first processing position, at which the first vessel is transportable to the first compartment of the rotor by the gripping device, transporting the first vessel to the first compartment of the rotor by the gripping device, and optionally inputting at least a second vessel into the processing chamber through the second input. The rotor can be rotated into the second processing position, at which the second vessel can be loaded into the second compartment of the rotor from the second input, if the second vessel is input. The method can also comprise rotating the rotor into the third processing position, at which the sample of the first vessel and/or the second vessel is aspirated by the pipetting device.

The method may further comprise rocking the first vessel and/or the second vessel. The gripping device may be moved along a first axis. The pipetting device may be moved along a second axis and along a third axis. The third axis can be different from the second axis. The third axis may be substantially perpendicular to the second axis. The second axis may be substantially parallel to the first axis. Alternatively, the pipetting device may be moved along the first axis. For example, the pipetting device can be moved together with the gripping device along the first axis. The method may further comprise dispensing the sample of the first vessel and/or the second vessel at a processing station within the processing chamber. The processing station may located spaced apart from the rotor or can be arranged on the rotor. The method may further comprise automatically transporting at least the first vessel to the gripping device. The method may further comprise manually loading the second vessel into the second compartment from the second input.

The apparatus for processing at least one sample as described can comprise a processing chamber, a first input for inputting at least a first vessel into the processing chamber, a second input for inputting at least a second vessel into the processing chamber, wherein the second input is different from the first input, a rotor comprising at least a first compartment for receiving the first vessel from the first input and a second compartment for receiving the second vessel from the second input, a gripping device adapted to at least grip the first vessel and to transport the first vessel from the first input to the first compartment of the rotor, and a pipetting device adapted to at least pipette a sample from the first vessel and/or the second vessel, wherein the rotor is rotatable at least between a first processing position, at which the first vessel is transportable to the first compartment of the rotor by the gripping device, a second processing position, at which the second vessel is loadable into the second compartment of the rotor from the second input, and a third processing position, at which the sample of the first vessel and/or the second vessel is aspiratable by the pipetting device.

The second input can be located at the rotor.

The gripping device can be adapted to rock the first vessel and/or the second vessel. The gripping device can be moveable along a first axis.

The second compartment can be different from the first compartment.

The rotor can be rotatable around a rotational axis. The first compartment can be located at a first angular position with respect to the rotational axis. The second compartment can be located at a second angular position with respect to the rotational axis. The second angular position can be different from the first angular position.

The second compartment can be separated from the first compartment. The second compartment can be separated from the first compartment by a separating wall. The second compartment can be located adjacent the first compartment.

The pipetting device can be moveable along a second axis and along a third axis. The third axis can be different from the second axis. The third axis can be substantially perpendicular to the second axis. The second axis can be substantially parallel to the first axis.

The pipetting device can be moveable along the first axis. The pipetting device can be moveable together with the gripping device along the first axis. The pipetting device can be adapted to dispense the sample of the first vessel and/or the second vessel at a processing station within the processing chamber.

The processing station can be located spaced apart from the rotor or can be arranged on the rotor.

The rotor can be formed as a segment of a cylinder.

The processing chamber can comprise a closure. The closure can be adapted to selectively expose or block the second input.

The first input can comprise a transporting device for automatically transporting at least the first vessel. The transporting device can be linearly moveable. The transporting device can be adapted to transport a rack. The rack can be adapted to receive a plurality of vessels.

The rotor can comprise a plurality of compartments for receiving a plurality of vessels.

A method for processing at least one sample using an apparatus described above can comprise inputting at least a first vessel into the processing chamber through the first input, retrieving the first vessel from the first input by the gripping device, rotating the rotor into the first processing position, at which the first vessel is transportable to the first compartment of the rotor by the gripping device, transporting the first vessel to the first compartment of the rotor by the gripping device, optionally inputting at least a second vessel into the processing chamber through the second input, wherein the rotor is rotated into the second processing position, at which the second vessel is loadable into the second compartment of the rotor from the second input, if the second vessel is input, and rotating the rotor into the third processing position, at which the sample of the first vessel and/or the second vessel is aspirated by the pipetting device.

The method can further comprise rocking the first vessel and/or the second vessel.

The gripping device can be moved along a first axis.

The pipetting device can be moved along a second axis and along a third axis. The third axis can be different from the second axis. The third axis can be substantially perpendicular to the second axis. The second axis can be substantially parallel to the first axis. The pipetting device can be moved along the first axis. The pipetting device can be moved together with the gripping device along the first axis.

The method can further comprise dispensing the sample of the first vessel and/or the second vessel at a processing station within the processing chamber. The processing station can be located spaced apart from the rotor or can be arranged on the rotor.

The method can further comprise automatically transporting at least the first vessel to the gripping device.

The method can further comprise manually loading the second vessel into the second compartment from the second input.

Referring initially to FIG. 1, FIG. 1 shows a perspective view of an apparatus 100 for processing at least one sample according to a first embodiment. The apparatus 100 can comprise a processing chamber 102, a first input 104 into the processing chamber 102, a second input 106 the processing chamber 102, a rotor 108, a gripping device 110, and a pipetting device 112. The rotor 108, the gripping device 110, and the pipetting device 112 can be at least partially or completely arranged within the processing chamber 102.

The first input 104 can be adapted to allow inputting at least a first vessel 114 into the processing chamber 102. The second input 106 can be adapted to allow inputting at least a second vessel 116 (FIG. 11) into the processing chamber 102. The second input 106 can be different from the first input 104. The first vessel 114 and the second vessel 116 can be tubes. Each of the first vessel 114 and the second vessel 116 can store a sample therein. The second input 106 can be located at the rotor 108. The first input 104 can be spaced apart from the rotor 108. The first input 104 can comprise a transporting device 118 for automatically transporting at least the first vessel 114. The transporting device 118 can be linearly moveable. The transporting device 118 may be adapted to transport a rack 120. The rack 120 can be adapted to receive a plurality of vessels, and, in one embodiment, a plurality of first vessels 114. Alternatively, the first vessels 114 may be provided in so-called single tube carriers. A single tube carrier can be a device adapted to carry a single vessel which may be formed as a tube. Such single tube carriers may be transported in a row by the transporting device 118.

The rotor 108 can be formed as a segment of a cylinder. The rotor 108 can be rotatable around a rotational axis 122. The rotor 108 can comprise at least a first compartment 124 for receiving the first vessel 114 from the first input 104 and a second compartment 126 for receiving the second vessel 116 from the second input 106. The first compartment 124 and the second compartment 126 can be formed as depressions or blind holes. With other words, the first compartment 124 and the second compartment 126 can extend into an interior of the rotor 108 and may not protrude therefrom. In order to avoid a mixing of the positions for the first vessel 114 and the second vessel 116 on the rotor 108, the second compartment 126 can be different from the first compartment 124. In one embodiment, the first compartment 124 can be located at a first angular position 128 with respect to the rotational axis 122 and the second compartment 126 can be located at a second angular position 130 with respect to the rotational axis 122. The second angular position 130 can be different from the first angular position 128. For example, the first angular position 128 can be spaced apart from the second angular position at about 90° to about 200° around the rotational axis 122 such as, for example, about 180°. Thus, a loading of the second vessel 116 into the first compartment 124 by mistake can be prevented. The rotor 108 can be rotatable at least between a first processing position, at which the first vessel 114 can be transportable to the first compartment 124 of the rotor 108 by the gripping device 110, a second processing position, at which the second vessel 116 can be loadable into the second compartment 126 of the rotor 108 from the second input 106, and a third processing position, at which the sample of the first vessel 114 and/or the second vessel 116 can be aspiratable by the pipetting device 112.

The gripping device 110 can be adapted to at least grip the first vessel 114 and to transport the first vessel 114 from the first input 104 to the first compartment 124 of the rotor 108. For this purpose, the gripping device 110 can be moveable along a first axis 132. The gripping device 110 can be arranged on a first frame 134, which can define the first axis 132. The first frame 134 may comprise rails (not shown in detail) or the like, on which the gripping device 110 can be moveable. In one embodiment, the gripping device 110 can be moveable upwards and downwards along the first axis 132. The gripping device 110 can be adapted to rock the first vessel 114. The so-called rocking process can be a process where a vessel can be rocked or shaken. Thus, a sample stored in the vessel can be suspended. For this purpose, the gripping device 110 can be pivotally arranged on the first frame 134. For example, the gripping device 110 may be pivoted around a pivot 136. Alternatively or in addition, the gripping device 110 can be adapted to rock the second vessel 116.

The pipetting device 112 can be at least adapted to pipette a sample from the first vessel 114 and/or the second vessel 116. The pipetting process of the pipetting device 112 can include an aspirating process and a dispensing process of the sample. For this purpose, the pipetting device 112 can comprise a pipetting needle 138. The pipetting device 112 can be moveable along a second axis 140 and along a third axis 142. The third axis 142 can be different from the second axis 140. In one embodiment, the third axis 142 can be substantially perpendicular to the second axis 140. Further, the second axis 140 can be substantially parallel to the first axis 132. The pipetting device 112 can be arranged on a second frame 144, which can define the second axis 140. The second frame 144 may comprise rails (not shown in detail) or the like, on which the pipetting device 112 can be moveable. In one embodiment, the pipetting device 112 can be moveable upwards and downwards along the second axis 140. The second frame 144, in turn, can be moveably arranged on a third frame 146, which can define the third axis 142. The third frame 146 may comprise rails (not shown in detail) or the like, on which the second frame 144 can be moveable. In one embodiment, the second frame 144 can be moveable to the leftwards and rightwards along the third axis 142. Thus, the pipetting device 112 may be moved within a plane defined by the second axis 140 and the third axis 142.

The apparatus 100 can further comprise a processing station 148. The processing station 148 can be arranged within the processing chamber 102. In this embodiment, the processing station 148 can be located spaced apart from the rotor 108. The processing station 148 can be arranged within the operating range of the pipetting device 112. The pipetting device 112 can be adapted to dispense the sample of the first vessel 114 and/or the second vessel 116 at the processing station 148. In one embodiment, the processing station 148 can comprise three mixing chambers 150 and a washing station 152 for washing the pipetting needle 138. The mixing chambers 150 can be provided to be used within an analysis or any other processing of the sample from the first vessel 114 and/or the second vessel 116. For this purpose, the pipetting device 112 may dispense the sample from the first vessel 114 and/or the second vessel 116 to the mixing chambers 150. For example, the pipetting device 112 may evenly distribute the sample from the first vessel 114 and/or the second vessel 116 to the mixing chambers 150. The mixing chambers 150 may include a reagent or the like which can be used for the analysis or any other processing of the sample.

Figure 2:
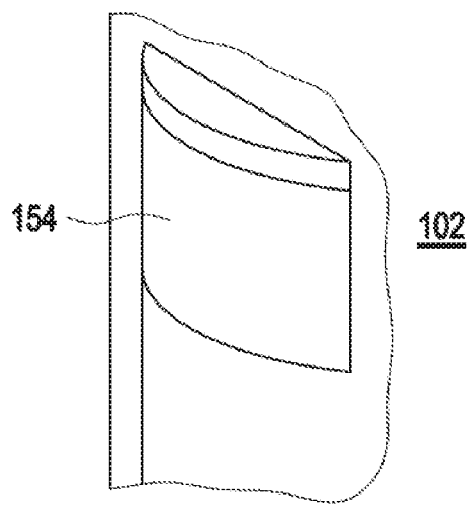
FIG. 2 illustrates a perspective view of a closure of the apparatus for processing at least one sample in a first operation position according to an embodiment of the present disclosure.

FIG. 2 shows a perspective view of a closure 154 of the apparatus 100 for processing at least one sample according to the first embodiment in a first operation position. The processing chamber 102 can comprise the closure 154. The closure 154 can be adapted to selectively expose or block the second input 106. The processing chamber 102 can comprise a button 156 for activating the closure 154. The button can be located at an outer surface thereof. In the first operation position, the closure 154 can block the second input 106. Thus, an operator may not load the second vessel 116 into the second compartment 126 of the rotor 108.

Figure 3:
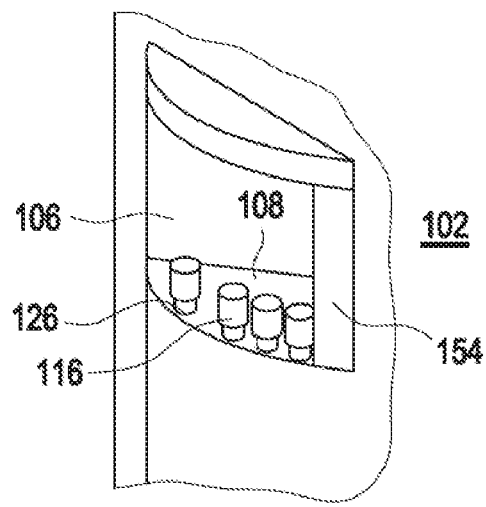
FIG. 3 illustrates a perspective view of the closure of the apparatus for processing at least one sample in a second operation position according to an embodiment of the present disclosure.

FIG. 3 shows a perspective view of the closure 154 of the apparatus 100 for processing at least one sample according to the first embodiment in a second operation position. In the second operation position, the closure 154 can expose the second input 106. Thus, an operator may load the second vessel 116 into the second compartment 126 of the rotor 108. The closure 154 can be moved between the first operation position and the second operation position by pressing the button 156. Normally, the closure 154 can be in the first operation position so as to block the second input 106, which can prevent an operator from access to the second input 106 during an operation of the apparatus 100. If the operator presses the button 156, the closure 154 can move into the second operation position so as to expose the second input 106, which can allow an operator to access the second input 106. For safety reasons, the closure 154 can be moved into the second operation position only if the operation of the apparatus 100 can allow, such as between the processing of two subsequent samples. In other words, the operator can be allowed to input the second vessel 116 only at suitable points in time of an operation of the apparatus 100.

The operation of the apparatus 100 will be described hereinafter with reference to FIGS. 1 to 13. The apparatus 100 can be used to process at least one sample. FIG. 1 shows a perspective view of the apparatus 100 in an operation position at the beginning. An operator of the apparatus 100 can load at least one first vessel 114 into the rack 120. The at least one first vessel 114 can comprise a first sample. The first sample may be whole blood. As shown in FIG. 1, the rack 120 may be used to be loaded with a plurality of first vessels 114.

Figure 4:
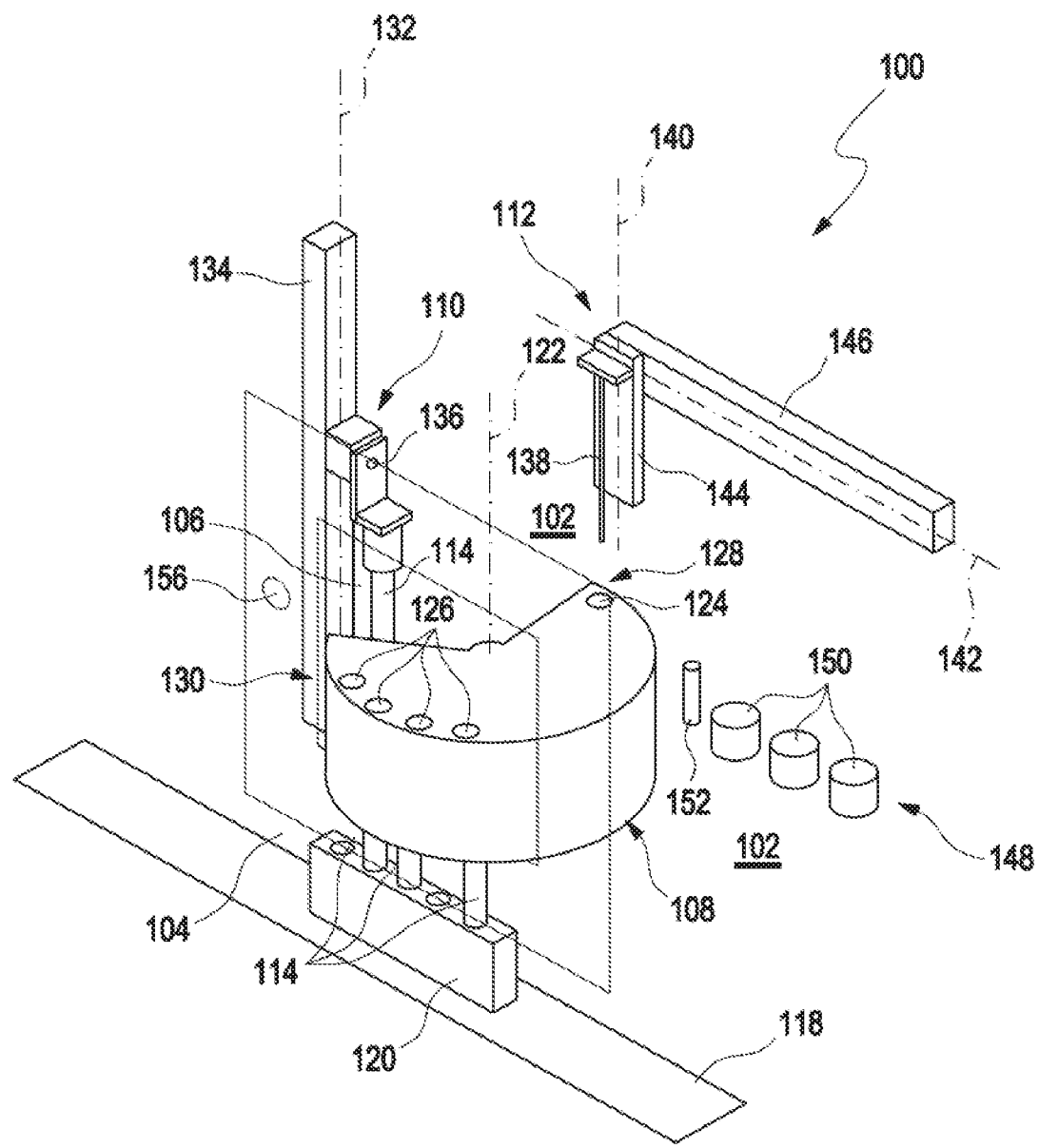
FIGS. 4-13 illustrate perspective views of the apparatus for processing at least one sample in different operation positions according to an embodiment of the present disclosure.

FIG. 4 shows a perspective view of the apparatus 100 in a subsequent operation position. After the rack 120 is loaded with the at least one first vessel 114, the rack 120 can be forwarded to the transporting device 118 at the first input 104. Then, the operator can activate the apparatus 100, for example by pressing a start button (not shown in detail). Then, the transporting device 118 can transport the rack 120 including the at least one first vessel 114 into the processing chamber 102 at a position where the rack 120 is in the operating range of the gripping device 110. The gripping device 110 can be moved downwards along the first axis 132 so as to retrieve the at least one first vessel 114 from the first input 104 and can grip the at least one first vessel 114.

Figure 5:
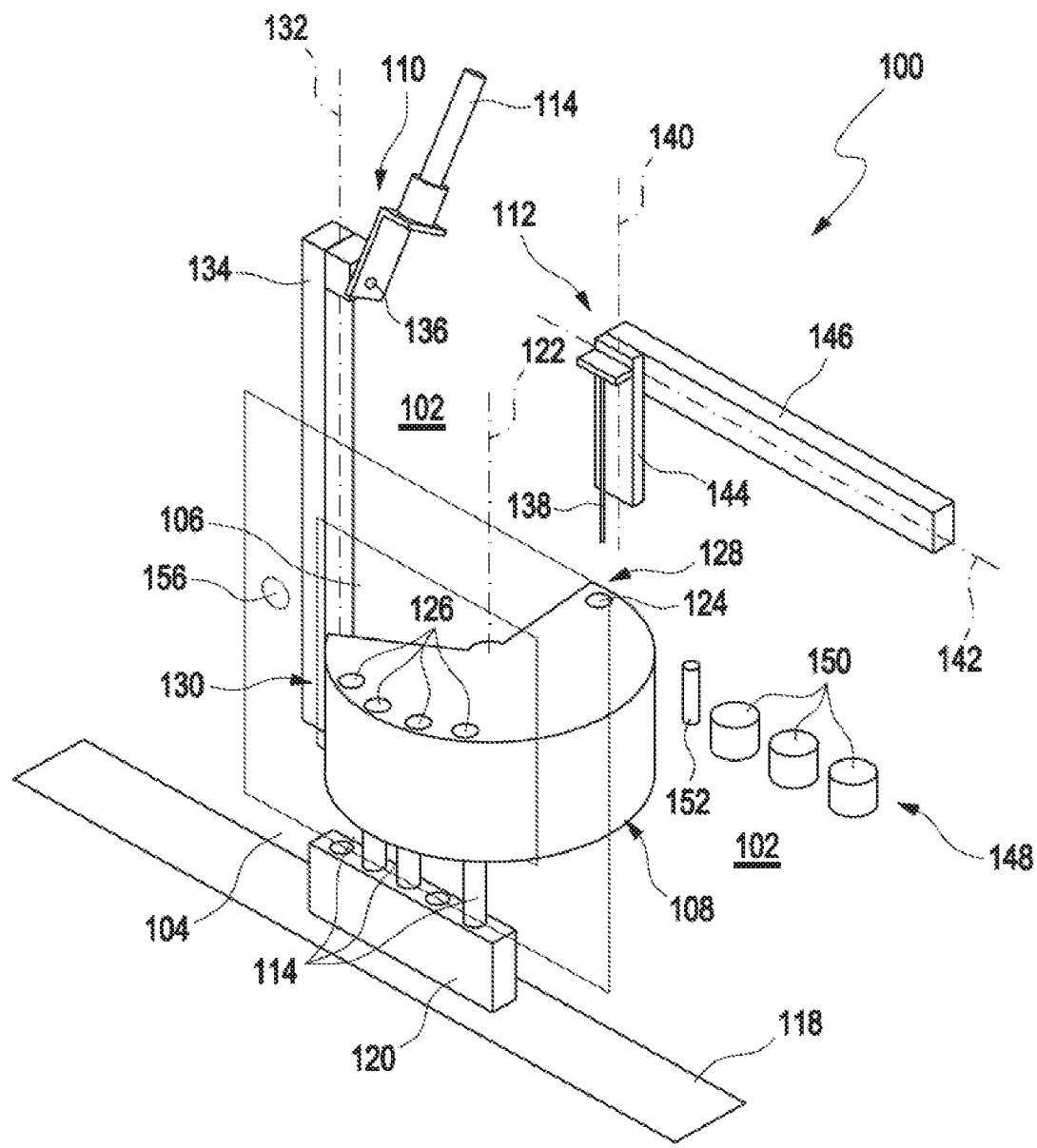

FIG. 5 shows a perspective view of the apparatus 100 in a subsequent operation position. The gripping device 110 can be moved upwards along the first axis 132 and can rock the first vessel 114.

Figure 6:
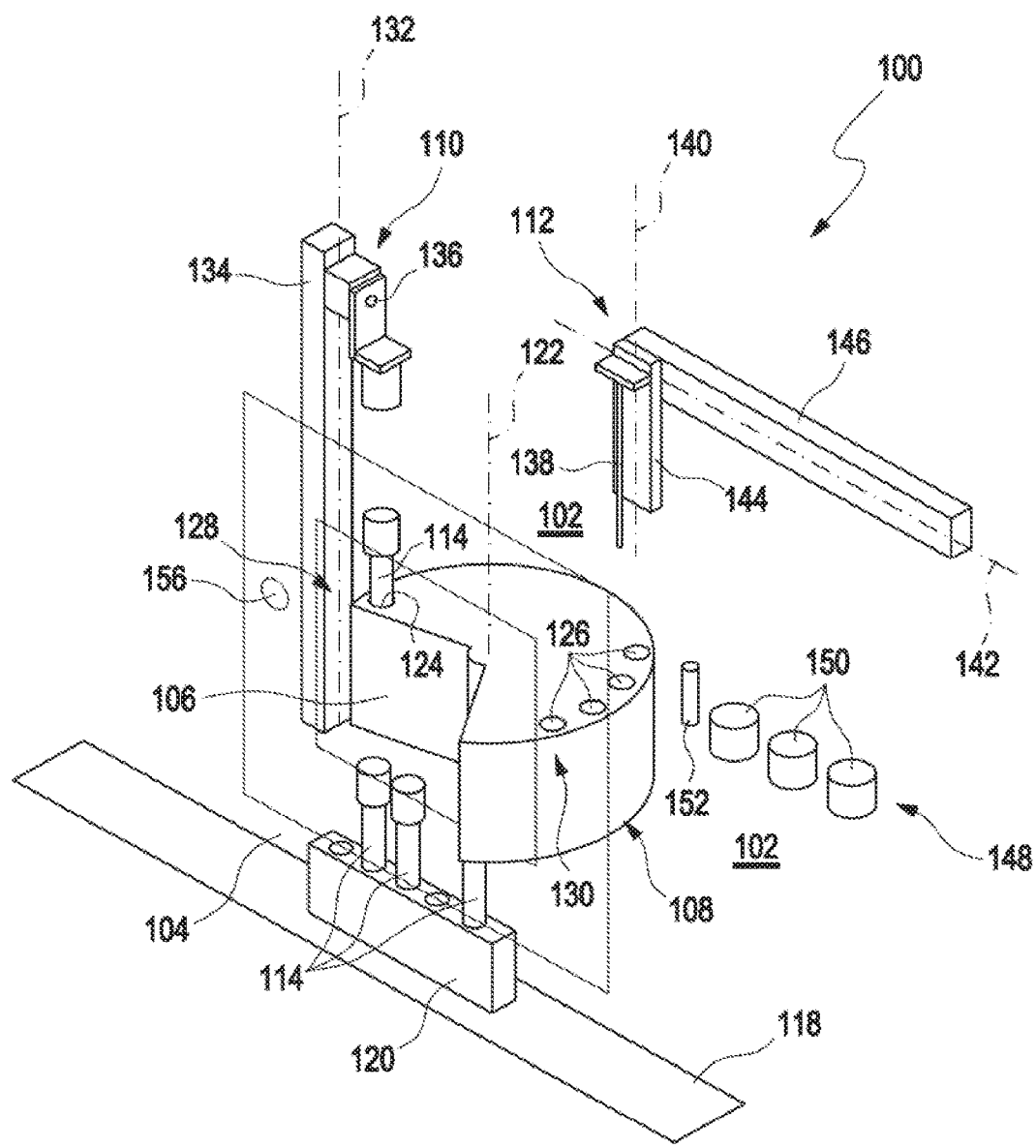

FIG. 6 shows a perspective view of the apparatus 100 in a subsequent operation position. The rotor 108 can be rotated into the first processing position. Thereafter, the gripping device 110 can transport the first vessel 114 to the first compartment 124 and can load the first vessel 114 therein.

Figure 7:
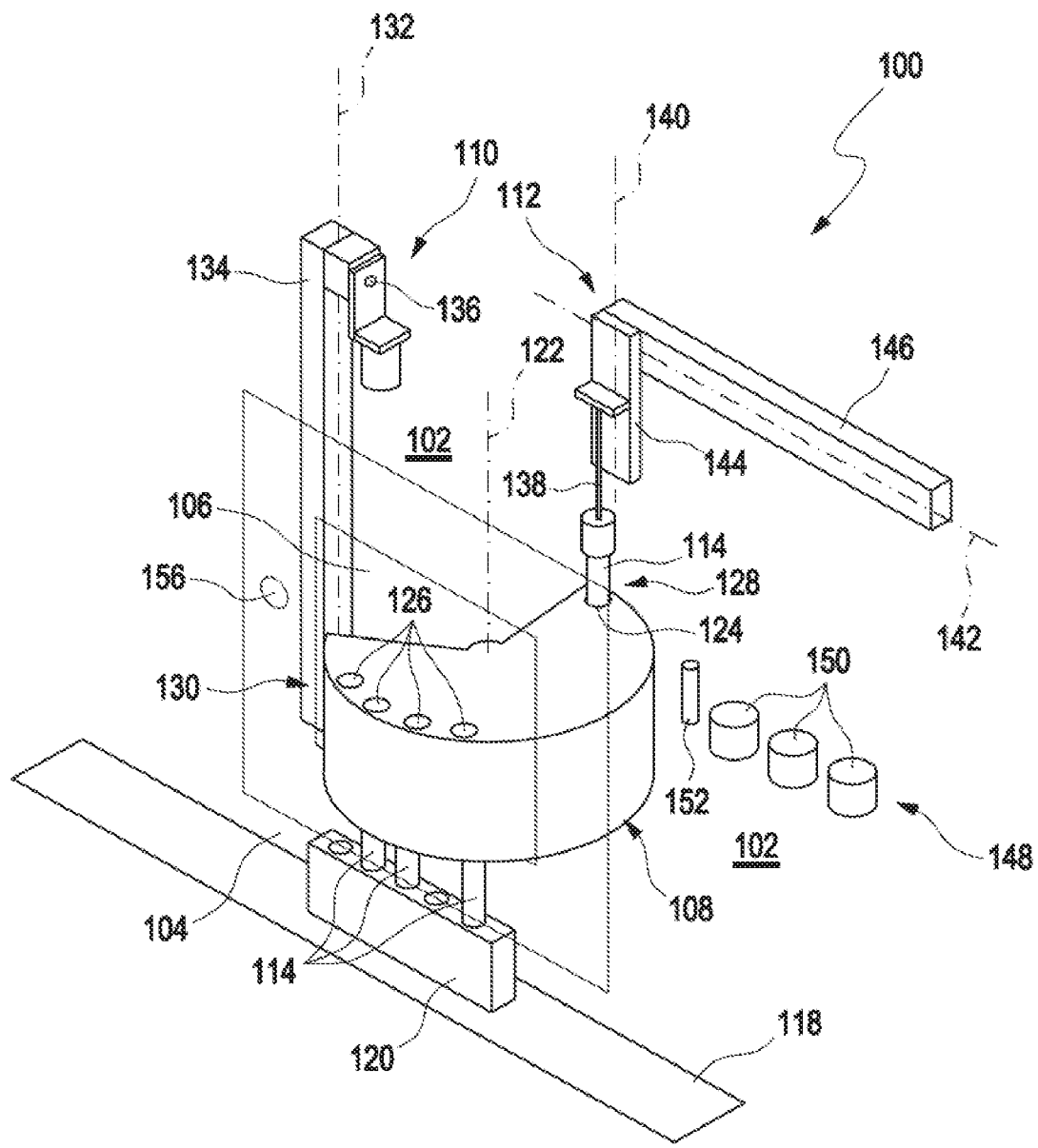

FIG. 7 shows a perspective view of the apparatus 100 in a subsequent operation position. The rotor 108 can be rotated into the third processing position such that the first vessel 114 can be located in the operating range of the pipetting device 112. The pipetting device 112 can be moved downwards along the second axis 140 and can aspirate the first sample.

Figure 8:
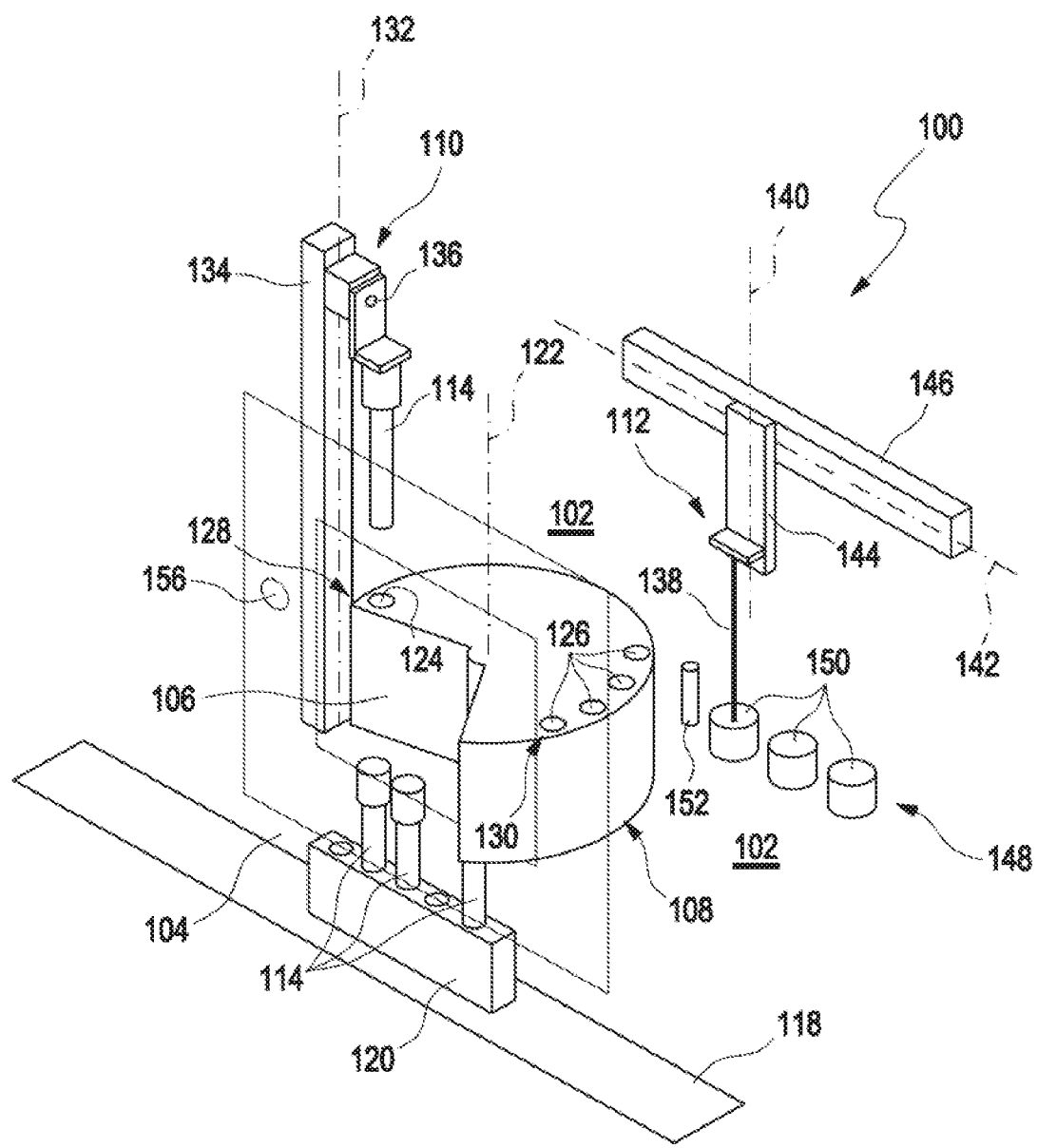

FIG. 8 shows a perspective view of the apparatus 100 in a subsequent operation position. Thereafter, the pipetting device 112 can be moved upwards along the second axis 140 and along the third axis 142. Thereby, the pipetting device 112 can be moved to the processing station 148. In the processing station 148, the pipetting device 112 can be moved downwards along the second axis 140 so as to insert the pipetting needle 138 into the washing station 152. Then, the pipetting device 112 can be moved upwards and downwards along the second axis 140 and laterally along the third axis 142 so as to dispense the first sample into the mixing chambers 150. The rotor 108 can be rotated back into the first processing position and the gripping device 110 can grip the first vessel 114 from the first compartment 124.

Figure 9:
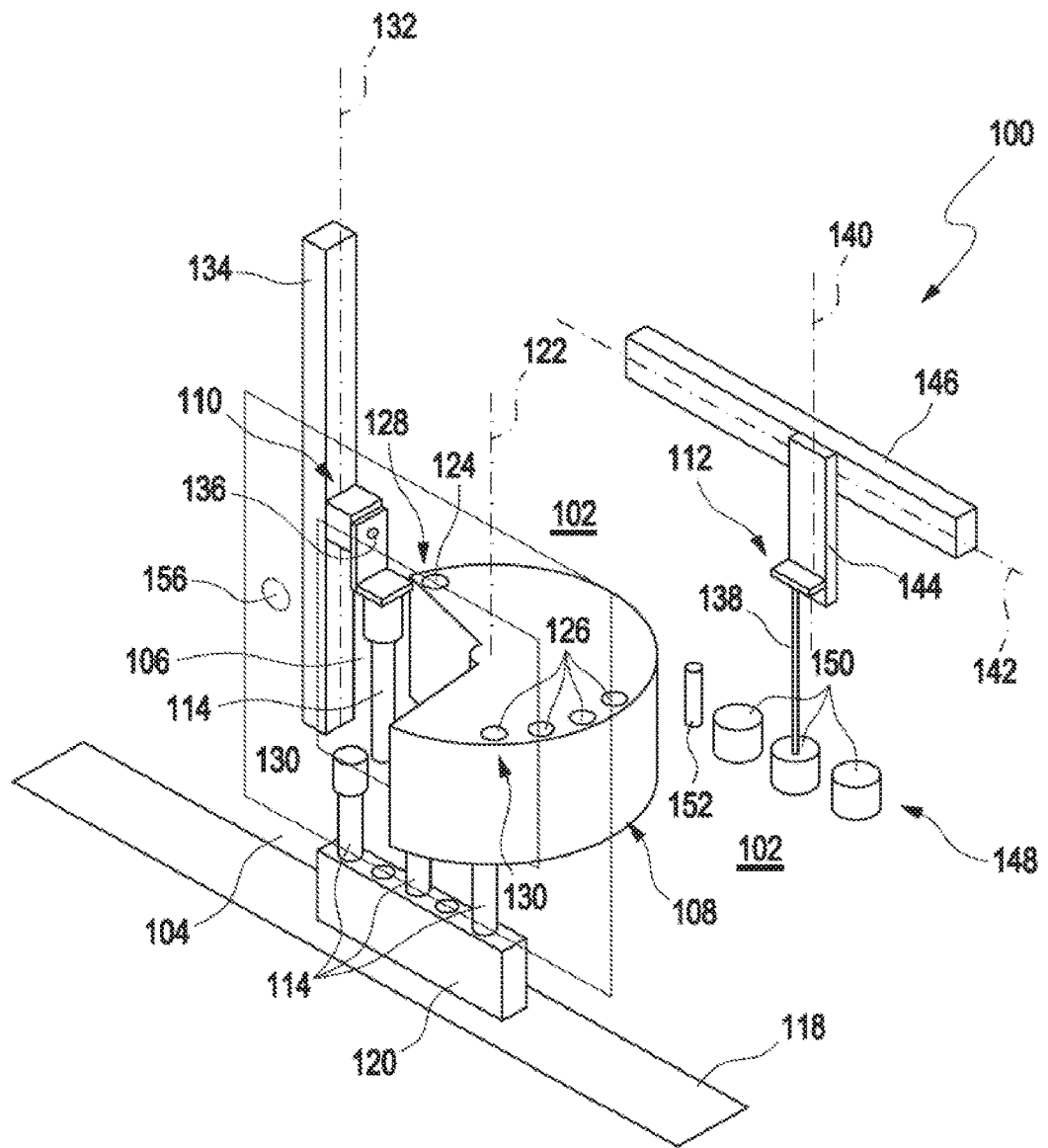

FIG. 9 shows a perspective view of the apparatus 100 in a subsequent operation position. The gripping device 110 can load the first vessel 114 back into the rack 120 while the pipetting device 112 can dispense the first sample into the respective mixing chambers 150. The transporting device 118 can transport the rack 120 one position further. The gripping device 110 can retrieve a subsequent, or second, one of the first vessels 114 from the first input 104 and can grip the at least one first vessel 114. This subsequent, or second, one of the first vessels 114 can be process as described before. Needless to say, all of the first vessels 114 supplied within the rack 120 may be process as described before.

Figure 10:
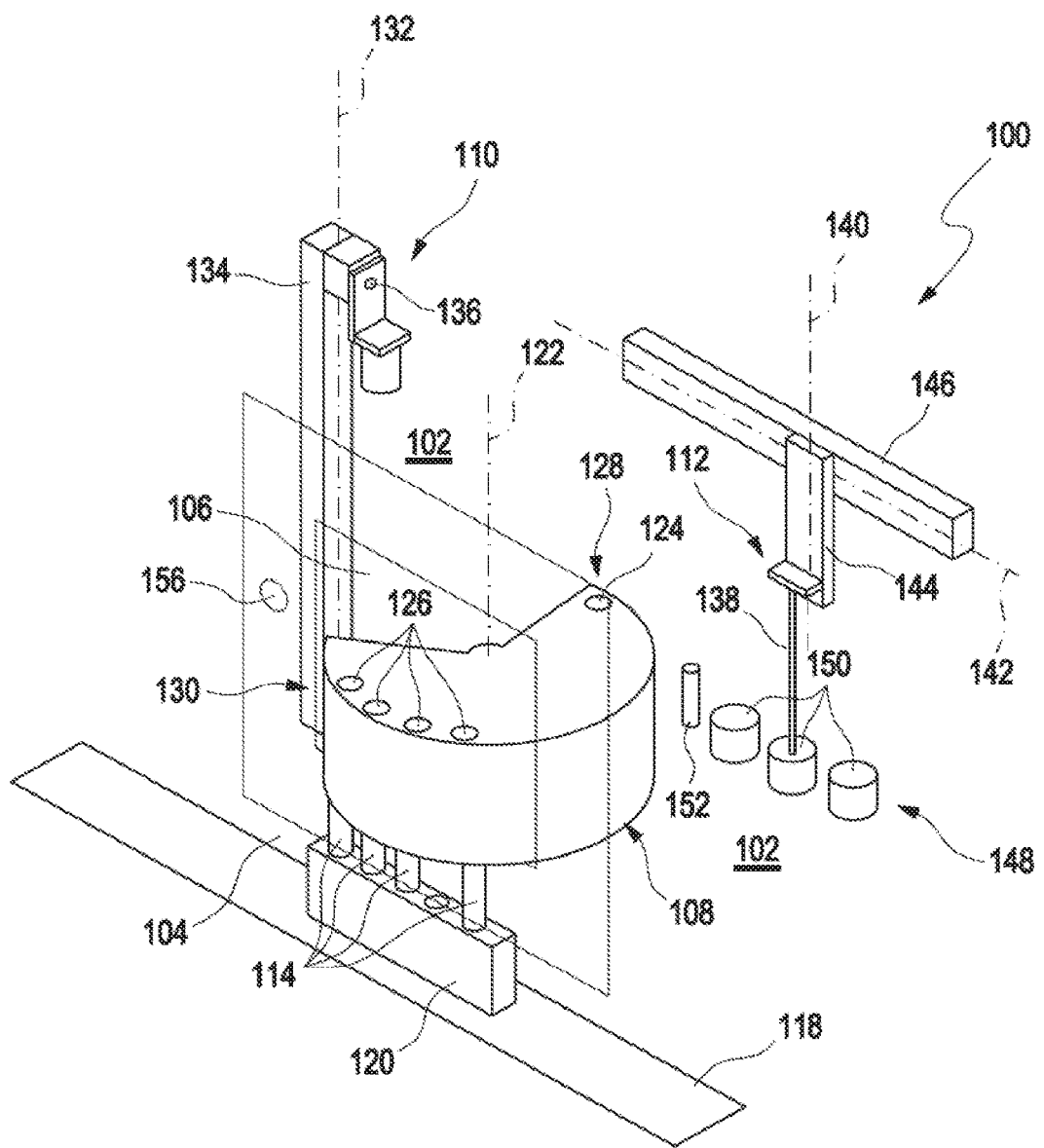
Figure 11:
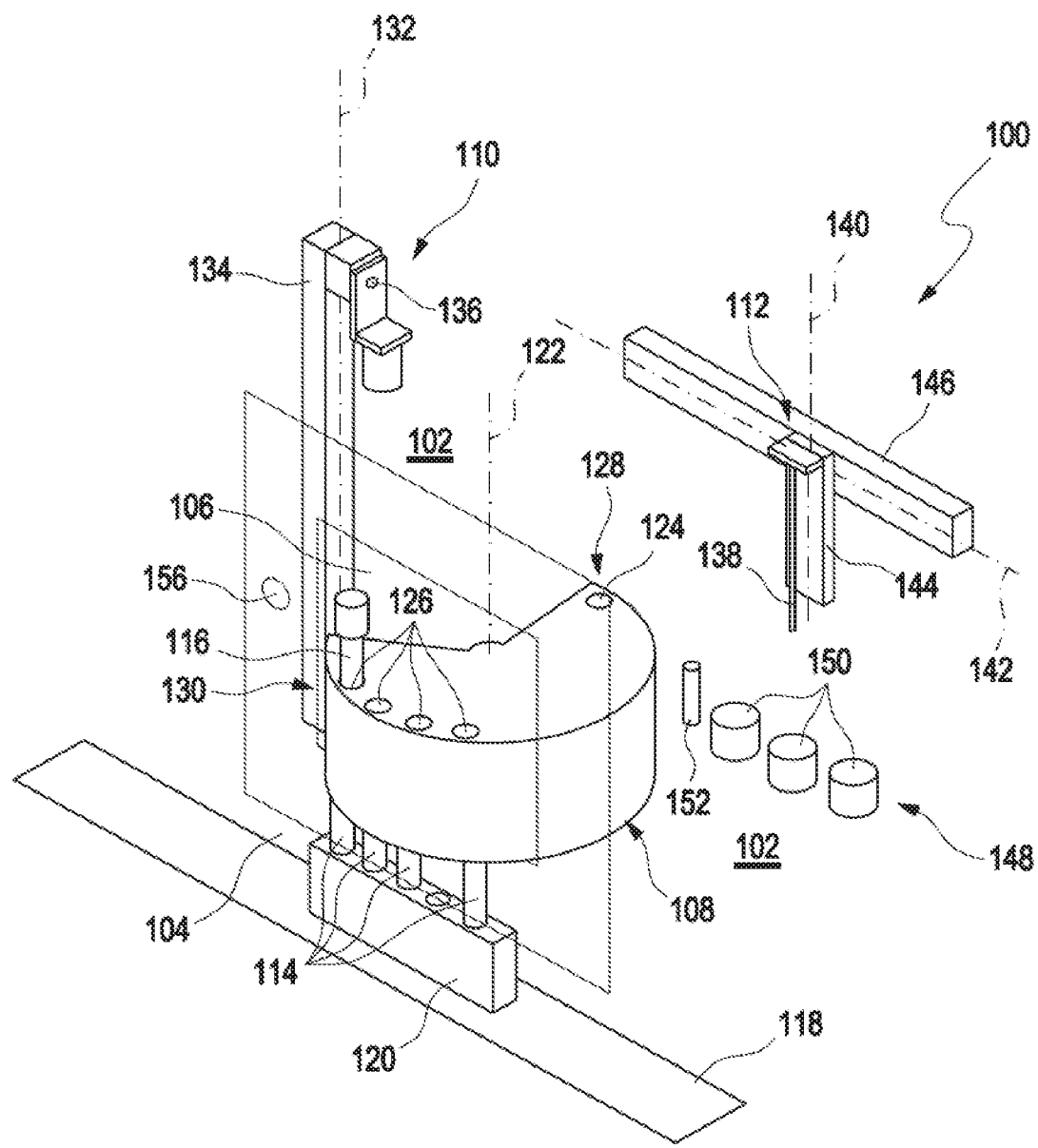

FIG. 10 shows a perspective view of the apparatus 100 in a further operation position. As the case may be, the operator may want to process a second sample stored in the second vessel 116. The second sample may be process as will be described in further detail hereinafter. The apparatus may start to process the second sample while the first sample from one of the first vessels 114 has not been finished to be process. For example, as indicated in FIG. 11, the apparatus 100 may start to process the second sample while the pipetting device 112 dispenses the first sample into the respective mixing chambers 150. If the operator wants to process a second sample stored in the second vessel 116, the operator can press the button 156 such that the closure 154 can expose the second input 106. During the processing of the first sample at the processing station 148, the rotor 108 can be rotated into the second processing position. In the second processing position, the second vessel 116 can be loadable into the second compartment 126 from the second input 106. The second vessel 116 can be manually loadable into the second compartment 126 from the second input 106 by the operator. It can be to be noted that the second sample stored in the second vessel 116 can be manually resuspended as the ingredients of whole blood sediment fast. Thus, a rocking of the second sample may be omitted.

Figure 12:
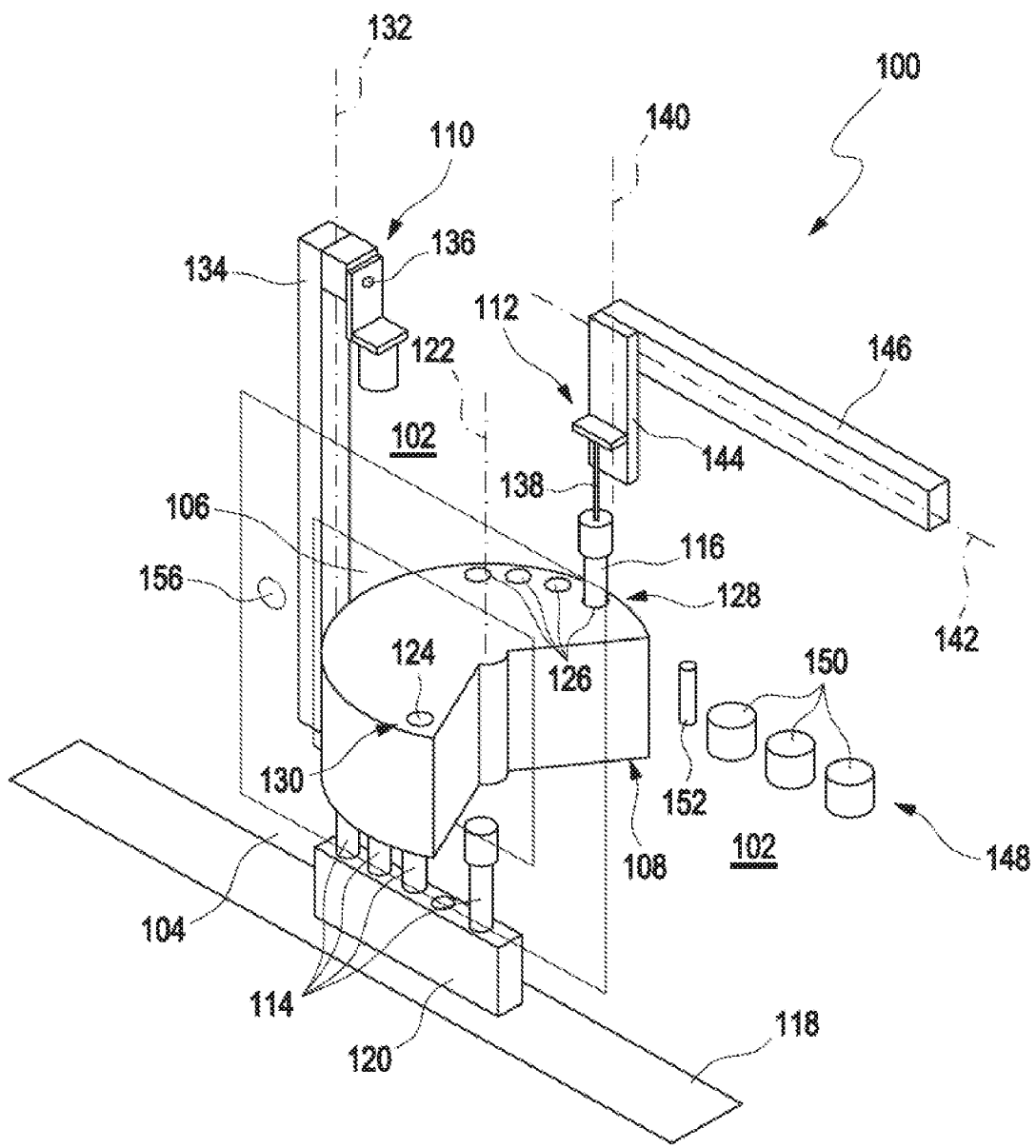

FIG. 11 shows a perspective view of the apparatus 100 in a subsequent operation position. FIG. 12 shows the second vessel 116 manually loaded into the second compartment 126 by the operator while the first sample from the first vessel 114 is dispensed into the mixing chambers 150 by the pipetting device 112. If the entire first sample is dispensed into the mixing chambers 150, the pipetting device 112 can be moved again to the washing station 152 so as to wash the pipetting needle 138.

FIG. 12 shows a perspective view of the apparatus 100 in a subsequent operation position. The rotor 108 can be rotated into the third processing position such that the pipetting device 112 may aspirate the second sample from the second vessel 116 in a manner identical to the operation with the first sample described before.

Figure 13:
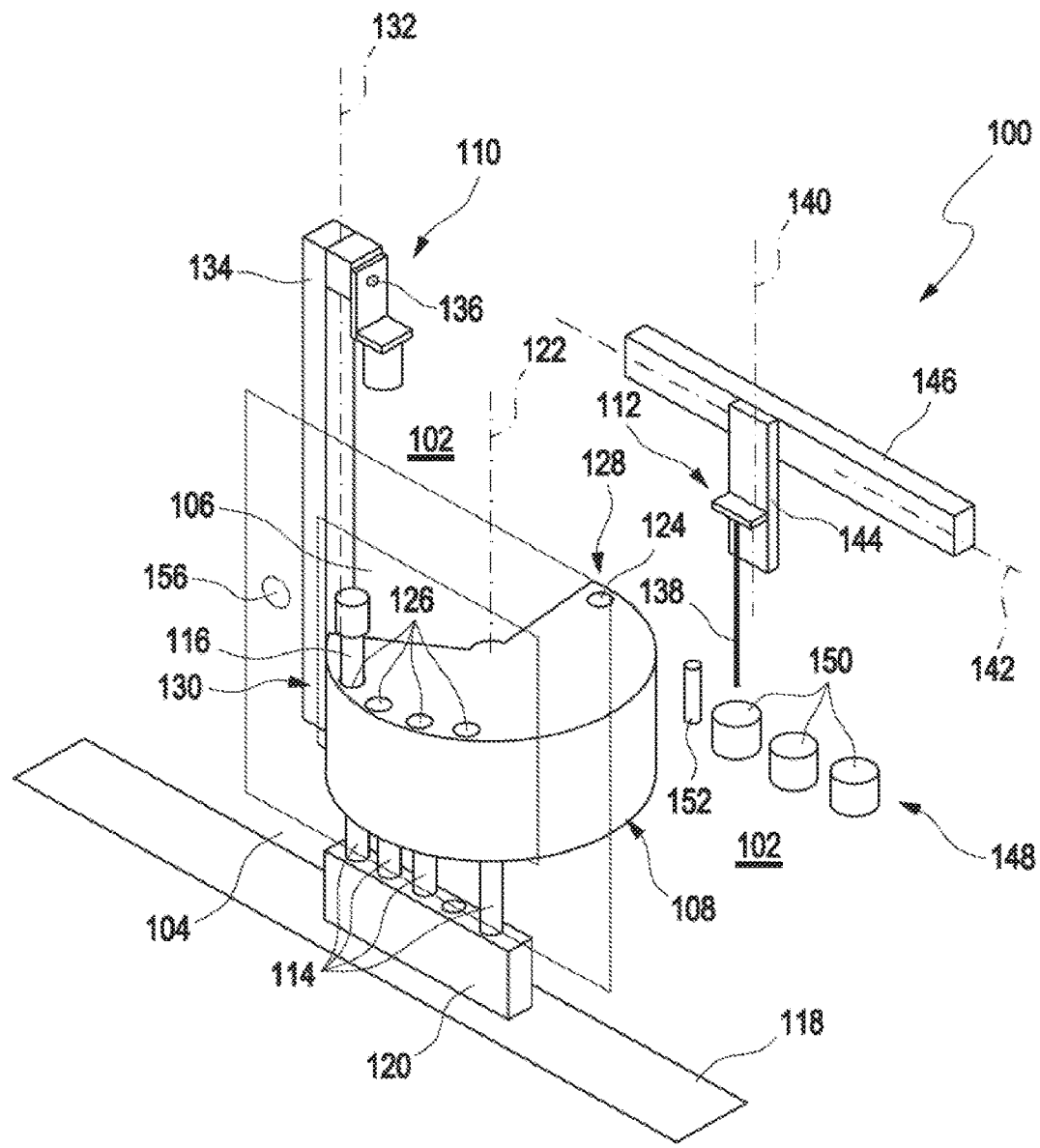

FIG. 13 shows a perspective view of the apparatus 100 in a subsequent operation position. The second sample 116 can then be processed by the pipetting device 112 similarly to the first sample, i.e. dispensed into the mixing chambers 150. Further, the rotor 108 can be rotated back into the second processing position such the operator may remove the second vessel 116 from the second compartment 126. Needless to say, the operator may wish to process more than one second vessel 116 such that the rotor 108 may comprise a plurality of second compartments 126 even though the number of second compartments 126 may not be too high as particularly ingredients of whole blood sediment fast. After the second sample is processed in the processing station 148, the apparatus 100 can further process any samples introduced through the first input 104 and provided by the rack 120.

Figure 14:
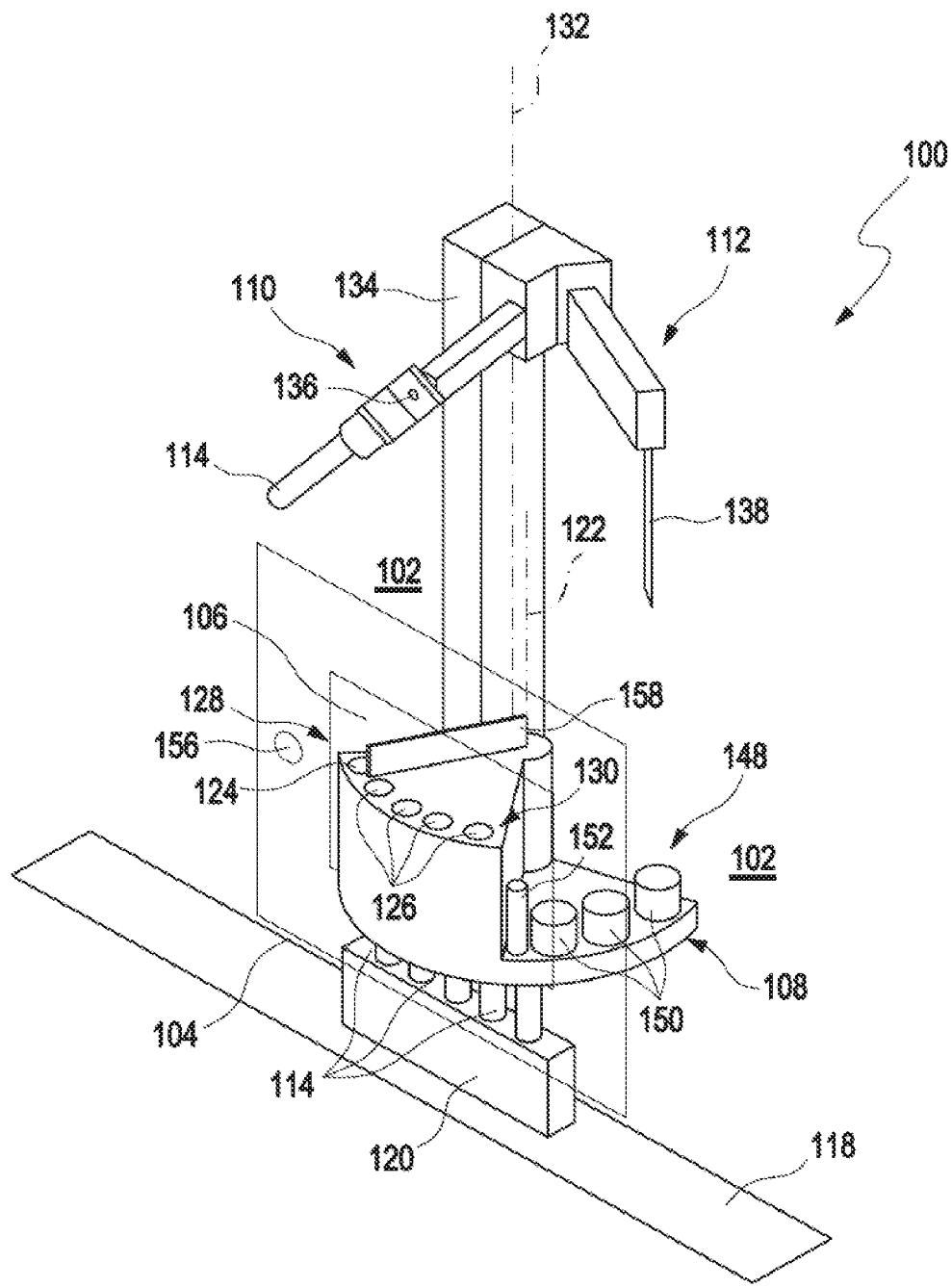
FIG. 14 illustrates a perspective view of an apparatus for processing at least one sample according to a second embodiment of the present disclosure.

FIG. 14 shows a perspective view of an apparatus 100 for processing at least one sample according to a second embodiment. Hereinafter, only the differences from the first embodiment will be described and like constructional members are indicated by like reference numbers. According to the second embodiment, the pipetting device 112 can be arranged at the first frame 134 so as to be movable along the first axis 132. The pipetting device 112 can be movable together with a gripping device 110 along the first axis 132. The second compartment 126 can be separated from the first compartment 124 by a separating wall 158. The rotor 108 of the second embodiment can be smaller if seen in a circumferential direction around the rotational axis 122 if compared to the rotor 108 of the first embodiment. Further, the processing station 148 can be arranged on the rotor 108.

Figure 15:
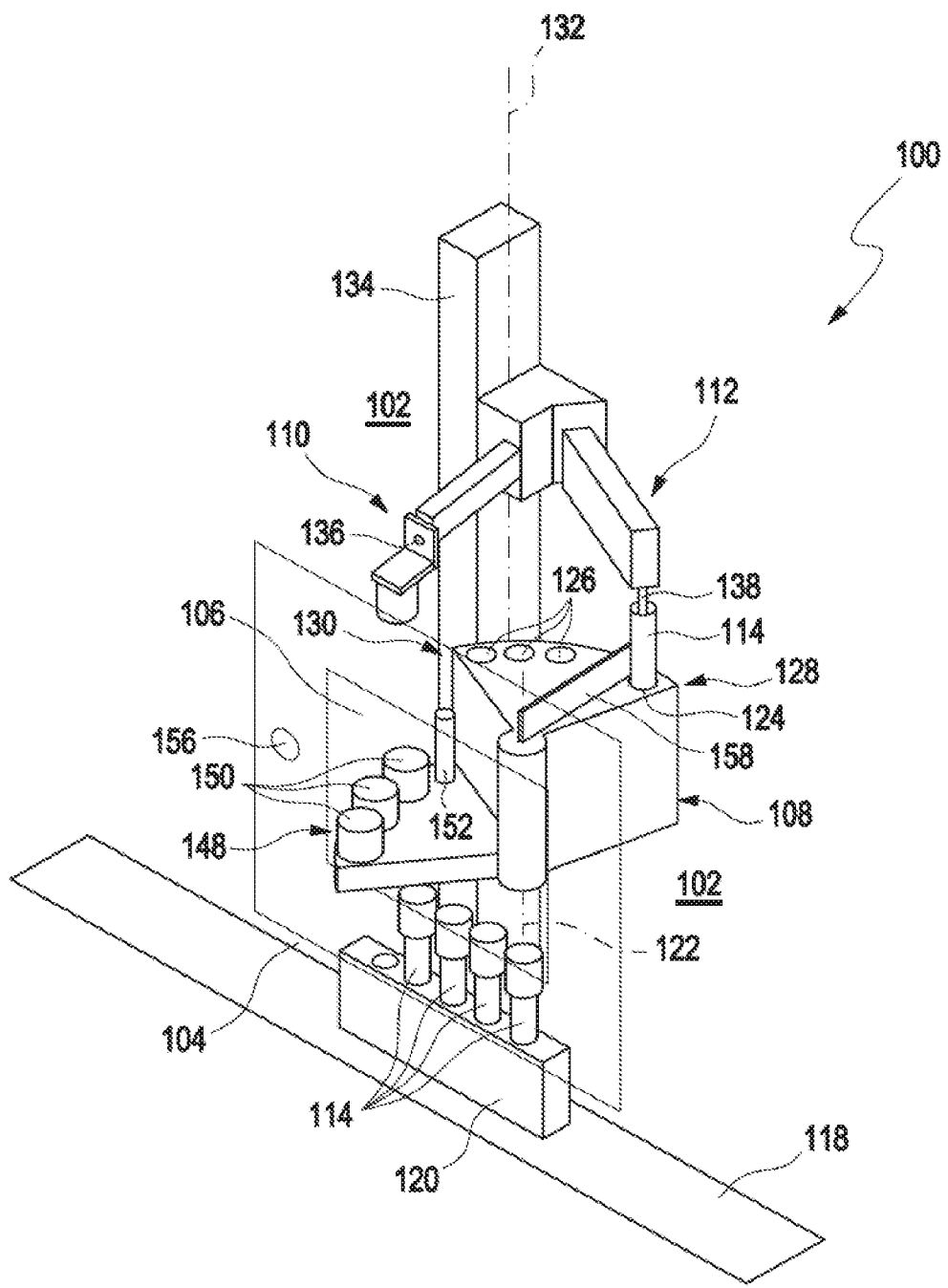
FIG. 15 illustrates another perspective view of the apparatus for processing at least one sample according to the second embodiment of the present disclosure.

FIG. 15 shows another perspective view of the apparatus 100 for processing at least one sample according to the second embodiment. As shown in FIG. 15, the pipetting device 112 may aspirate a sample from the first vessel 114 being loaded into the first compartment 124.

Figure 16:
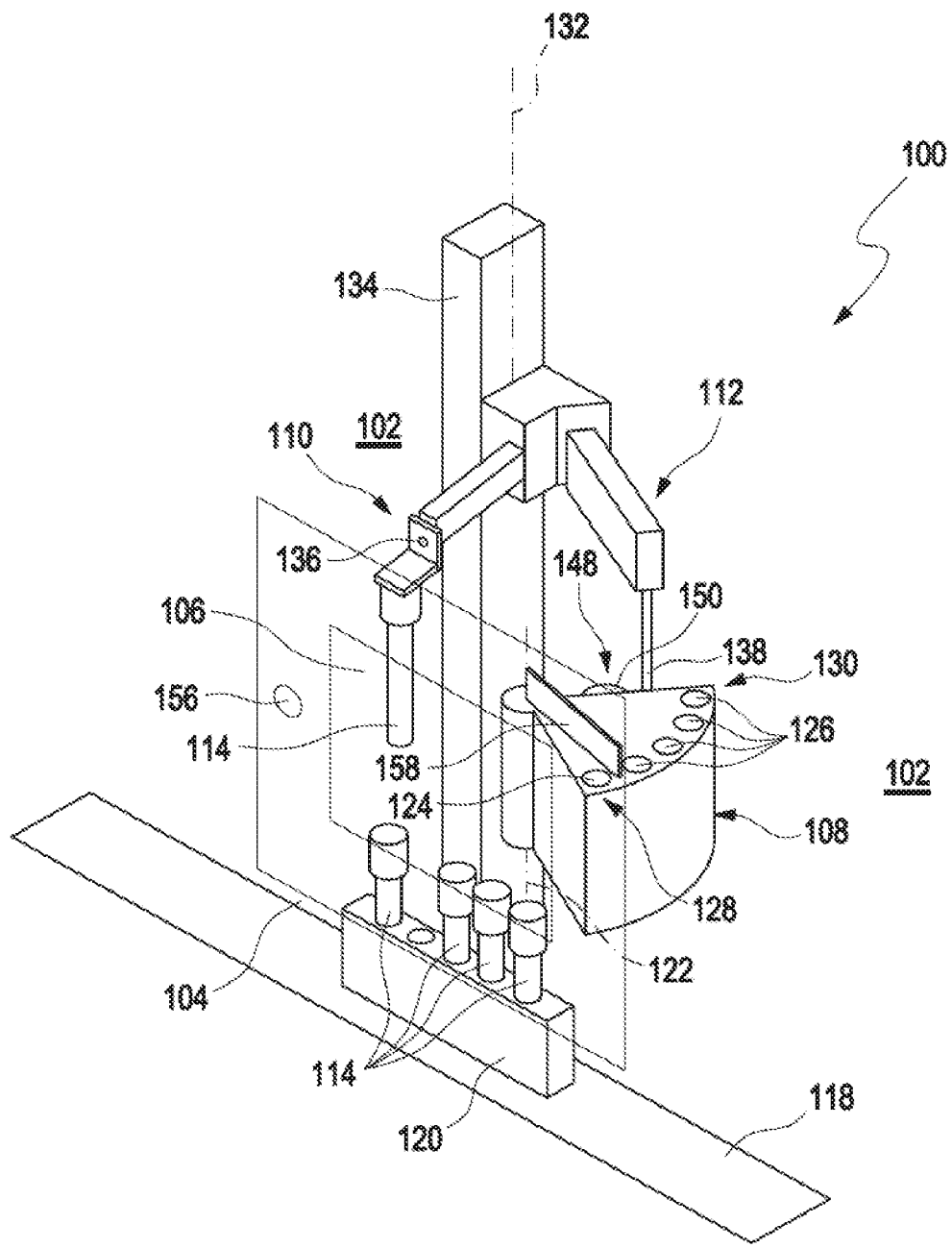
FIG. 16 illustrates another perspective view of the apparatus for processing at least one sample according to the second embodiment of the present disclosure.

FIG. 16 shows another perspective view of the apparatus 100 for processing at least one sample according to the second embodiment. As shown in FIG. 16, while the pipetting device 112 dispenses the sample from the first vessel 114 into the mixing chambers 150 of the processing station 148, the gripping device 110 may grip a further first vessel 114 from the rack 120.

The operation principle can basically be the same as with the first embodiment except for the common movement of the gripping device 110 and the pipetting device 112 as will be explained in further detail below. The operation of the apparatus 100 can be described hereinafter with reference to FIGS. 14 to 16. As shown in FIG. 14, the rack 120 may be used to be loaded with a plurality of first vessels 114. After the rack 120 is loaded with the at least one first vessel 114, the rack 120 can be forwarded to the transporting device 118 of the first input 104. Then, the operator can activate the apparatus 100, for example by pressing a start button (not shown in detail). Then, the transporting device 118 can transport the rack 120 including the at least one first vessel 114 into the processing chamber 102 at a position where the rack 120 can be in the operating range of the gripping device 110. The rotor 108 can be rotated into the first processing position. The gripping device 110 and the pipetting device 112 can be moved downwards along the first axis 132. The gripping device 110 can grip the at least one first vessel 114. Then, the gripping device 110 and the pipetting device 112 can be moved upwards along the first axis 132. The gripping device 110 can rock the first vessel 114. Thereafter, the gripping device 110 can transport the first vessel 114 to the first compartment 124 and can load the first vessel 114 therein. Then, the rotor 108 can be rotated into the third processing position such that the first vessel 114 can be located in the operating range of the pipetting device 112. The gripping device 110 and the pipetting device 112 can be moved downwards along the first axis 132. The pipetting device 112 can aspirate the first sample. Thereafter, the gripping device 110 and the pipetting device 112 can be moved upwards along the first axis 132. The rotor 108 can be rotated such that the processing station 148 can move into the operating range of the pipetting device 112. Subsequently, the gripping device 110 and pipetting device 112 can be moved downwards and upwards in a repeated manner along the first axis 132 so as to insert the pipetting needle 138 into the washing station 152 to dispense the first sample into the mixing chambers 150. During the repeated downwards and upwards movements of the gripping device 110 and the pipetting device 112, the rotor 108 can be rotated further step by step so as to move the washing station 152 and the mixing chambers 150 into the operating range of the pipetting device 112 as the washing station 152 and the mixing chambers 150 can be arranged on a circular path around the rotational axis 122 on the rotor 108. Further, during these repeated downwards and upwards movements of the gripping device 110 and the pipetting device 112, the gripping device 110 may grip the next first vessel 114 and rock the same. The rotor 108 of the second embodiment can be smaller if seen in a circumferential direction around the rotational axis 122 if compared to the rotor 108 of the first embodiment in order to prevent any collision of the gripping device 110 and the pipetting device 112 with the rotor 108 during the movements thereof.

As the case may be, the operator may want to process a second sample stored in the second vessel 116. If this is the case, the operator can press the button 156 such that the closure 154 can expose the second input 106. The processing of the second sample stored in the second vessel 116 can be the same as with the first embodiment such that the description thereof is omitted.

It is noted that terms like "preferably," "commonly," and "typically" are not utilized herein to limit the scope of the claimed embodiments or to imply that certain features are critical, essential, or even important to the structure or function of the claimed embodiments. Rather, these terms are merely intended to highlight alternative or additional features that may or may not be utilized in a particular embodiment of the present disclosure.

For the purposes of describing and defining the present disclosure, it is noted that the term "substantially" is utilized herein to represent the inherent degree of uncertainty that may be attributed to any quantitative comparison, value, measurement, or other representation. The term "substantially" is also utilized herein to represent the degree by which a quantitative representation may vary from a stated reference without resulting in a change in the basic function of the subject matter at issue.

Having described the present disclosure in detail and by reference to specific embodiments thereof, it will be apparent that modifications and variations are possible without departing from the scope of the disclosure defined in the appended claims. More specifically, although some aspects of the present disclosure are identified herein as preferred or particularly advantageous, it is contemplated that the present disclosure is not necessarily limited to these preferred aspects of the disclosure.

I claim:

1. An apparatus for processing at least one sample, the apparatus comprising:
   a processing chamber;
   a first input for inputting at least a first vessel into the processing chamber;
   a second input for inputting at least a second vessel into the processing chamber, wherein the second input is different from the first input;
   a rotor, wherein the rotor is formed as a segment of a cylinder, the rotor comprising at least a first compartment located at a first angular position along the rotor cylinder for receiving the first vessel from the first input and a second compartment located at a second angular position along the rotor cylinder for receiving the second vessel from the second input;
   a gripping device adapted to at least grip the first vessel and to transport the first vessel from the first input to the first compartment of the rotor; and
   a pipetting device adapted to at least pipette a sample from the first vessel and/or the second vessel, wherein the rotor is rotatable at least between a first processing position, at which the first vessel is transportable to the first compartment of the rotor by the gripping device, a second processing position, at which the second vessel is loadable into the second compartment of the rotor from the second input, and a third processing position, at which the sample of the first vessel and/or the second vessel is aspiratable by the pipetting device.

2. The apparatus according to claim 1, wherein the second input is located at the rotor.

3. The apparatus according to claim 1, wherein the gripping device is adapted to rock the first vessel and/or the second vessel.

4. The apparatus according to claim 1, wherein the gripping device is moveable along a first axis.

5. The apparatus according to claim 1, wherein the second compartment is different from the first compartment.

6. The apparatus according to claim 5, wherein the rotor is rotatable around a rotational axis.

7. The apparatus according to claim 6, wherein the first compartment is located at a first angular position with respect to the rotational axis and wherein the second compartment is located at a second angular position with respect to the rotational axis.

8. The apparatus according to claim 7, wherein the second angular position is different from the first angular position.

9. The apparatus according to claim 1, wherein the second compartment is separated from the first compartment.

10. The apparatus according to claim 9, wherein the second compartment is separated from the first compartment by a separating wall.

11. The apparatus according to claim 1, wherein the pipetting device is moveable together with the gripping device along the first axis.

12. The apparatus according to claim 1, wherein the processing chamber comprising a closure.

13. The apparatus according to claim 12, wherein the closure is adapted to selectively expose or block the second input.

14. The apparatus according to claim 1, wherein the first input comprising a transporting device for automatically transporting at least the first vessel.

15. A method for processing at least one sample using an apparatus according to claim 1, the method comprising:
    inputting at least a first vessel into the processing chamber through the first input;
    retrieving the first from the first input by the gripping device;
    rotating the rotor into the first processing position, at which the first vessel is transportable to the first compartment of the rotor by the gripping device;
    transporting the first vessel to the first compartment of the rotor by the gripping device;
    inputting at least a second vessel into the processing chamber through the second input, wherein the rotor is rotated into the second processing position, at which the second vessel is loadable into the second compartment of the rotor from the second input, if the second vessel is input; and
    rotating the rotor into the third processing position, at which the sample of the first vessel and/or the second vessel is aspirated by the pipetting device.

16. The method according to claim 15, further comprising,
    rocking the first vessel and/or the second vessel.

17. The method according to claim 15, further comprising,
    manually loading the second vessel into the second compartment from the second input.

* * * * *